(12) United States Patent
Avinash et al.

(10) Patent No.: US 6,917,697 B2
(45) Date of Patent: Jul. 12, 2005

(54) METHOD AND APPARATUS TO AUTOMATICALLY DETERMINE TISSUE CANCELLATION PARAMETERS IN X-RAY DUAL ENERGY IMAGING

(75) Inventors: Gopal B. Avinash, New Berlin, WI (US); John Michael Sabol, Sussex, WI (US); Francois Serge Nicolas, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 670 days.

(21) Appl. No.: 09/681,611

(22) Filed: May 8, 2001

(65) Prior Publication Data

US 2002/0186872 A1 Dec. 12, 2002

(51) Int. Cl.[7] .......................... G06K 9/00; G01N 23/06
(52) U.S. Cl. ................ 382/132; 378/98.11; 378/98.12; 378/53
(58) Field of Search ........................... 382/132; 378/62, 378/98.11, 98.9, 98.12, 16, 53, 57, 5

(56) References Cited

U.S. PATENT DOCUMENTS

| | | | | |
|---|---|---|---|---|
| 4,355,331 A | * | 10/1982 | Georges et al. | 378/98.11 |
| 4,499,493 A | * | 2/1985 | Nishimura | 378/98.9 |
| 4,792,900 A | * | 12/1988 | Sones et al. | 600/407 |
| 5,301,107 A | * | 4/1994 | Shimura | 378/51 |
| 5,402,338 A | * | 3/1995 | Ito | 600/407 |
| 5,838,758 A | * | 11/1998 | Krug et al. | 378/53 |
| 6,173,034 B1 | * | 1/2001 | Chao | 378/37 |
| 6,205,348 B1 | * | 3/2001 | Giger et al. | 600/407 |
| 6,343,111 B1 | * | 1/2002 | Avinash et al. | 378/98.11 |
| 6,597,759 B2 | * | 7/2003 | Mazess et al. | 378/53 |

OTHER PUBLICATIONS

"Active Dual Energy X–Ray Detector: Experimental Characterization", Alvarez et al., Medical Imaging 1997: Physics of Medical Imaging, May 12, 1997, p. 419–426.

"Experimental Comparison of Dual Energy X–ray Detectors", Alvarez et al., Medical Imaging 1996: Physics of Medical Imaging, May 7, 1996, p. 534–543.

"Generalized Image Combinations in Dual KVP Digital Radiography", Lehmann et al., Medical Physics, vol. 8, No. 5, Sep./Oct. 1981, p. 659–667.

"Single–Exposure Dual–Energy Computed Radiography", Stewart et al., Medical Physics, vol. 17, No. 5, Sep./Oct. 1990, p. 866–875.

* cited by examiner

*Primary Examiner*—Brian Werner
*Assistant Examiner*—Shefali Patel
(74) *Attorney, Agent, or Firm*—McAndrews, Held & Malloy, Ltd.; Peter I. Vogel; Michael A. Dellapenna

(57) ABSTRACT

A method is provided to automatically determine a structure cancelled image in a dual energy decomposition system. A high energy and a low energy level image of internal anatomy formed of at least first and second types of structure are acquired. A characteristic mask is computed using a gradient mask and a localization mask. A first cancellation parameter is evaluated against the characteristic mask, and a second cancellation parameter is computed based upon the first cancellation parameter. The first or second cancellation parameter is selected from a range in a look-up table determined by an effective kVp used to acquire the high level image and an effective kVp used to acquire the low level image. An image of soft structure and an image of hard structure are obtained from the first and second energy level images according to a cancellation equation using the first and second cancellation parameters.

28 Claims, 5 Drawing Sheets

METHOD AND APPARATUS TO AUTOMATICALLY DETERMINE TISSUE CANCELLATION PARAMETERS IN X-RAY DUAL ENERGY IMAGING

BACKGROUND OF INVENTION

The preferred embodiments of the present invention relate to medical diagnostic X-ray imaging. In particular, the preferred embodiments of the present invention relate to dual energy decomposition for tissue specific imaging using a look-up table to obtain a range of cancellation parameters.

Today, doctors and technicians commonly have access to very sophisticated medical diagnostic X-ray imaging devices. Typically during the operation of an X-ray imaging device, an X-ray source emits X-ray photons under very controlled circumstances. The X-ray photons travel through a region of interest (ROI) of a patient under examination and impinge upon a detector. In the past, X-ray imaging devices employed rudimentary film based detectors. However, recent developments have led to solid state detectors comprised of a grid of discrete detector elements that individually respond to exposure by X-ray photons.

Regardless of the detector used, however, the goal remains the same, namely to produce a clear resultant image of preselected structures of interest (e.g., specific types of tissues) within the ROI.

There is an inherent difficulty associated with producing a clear resultant image, however. In particular, because the X-ray photons travel through the entire patient, the image formed on the detector is a superposition of all the anatomic structures through which X-ray photons pass, including the preselected structures of interest. The superposition of anatomic structures is sometimes referred to as "anatomic noise". The effect of anatomic noise on the resultant image is to produce clutter, shadowing, and other obscuring effects that render the resultant image much less intelligible than the ideal clear resultant image.

Past attempts to reduce the effects of anatomic noise included, for example, "dual-energy" imaging. When employing dual-energy imaging, a doctor or technician acquired an image at high average X-ray photon energy, and an image at low average X-ray photon energy. Because different internal structures absorb different X-ray photon energies to different extents, it was possible to combine the two resultant images to suppress anatomic noise, according to:

$$SB(x,y) = \exp[\log(H(x,y)) - w \log(L(x,y))], \quad (0 < w < 1)$$

where SB is the decomposed image achieved through the log subtraction at a specific cancellation parameter w, H(x,y) is an image obtained at high energy, and L(x,y) is an image obtained at low energy. By varying w, SB becomes a decomposed image of either soft tissue or of bone.

However, in the past, users of the previously mentioned decomposition technique had to vary the cancellation parameter, w, manually through trial and error until the resultant image emphasized the soft tissue or bone of interest and de-emphasized the other. The resulting manual variation of the cancellation parameter in the log subtraction equation was time consuming and hindered the workflow in the clinical environment.

A need has long existed in the industry for a method and apparatus for dual energy decomposition that addresses the problems noted above and previously experienced.

SUMMARY OF INVENTION

In accordance with at least one preferred embodiment, a method is provided to automatically determine a structure cancelled image in a dual energy decomposition system. A high energy and a low energy level image of internal anatomy formed of at least first and second types of structure are acquired. A gradient mask is computed using an edge cancellation parameter and a gradient threshold. A localization mask is computed from a localization image based on either the low or the high energy image and compared with an intensity threshold automatically selected from a set based upon a selected diagnostic application. A characteristic mask is computed using the gradient mask and localization mask. A first cancellation parameter is evaluated against the characteristic mask, and a second cancellation parameter is computed based upon the first cancellation parameter. In accordance with at least one preferred embodiment, the first or second cancellation parameter is selected from a range in a look-up table determined by an effective kVp used to acquire the high level image and an effective kVp used to acquire the low level image. Hard and soft structure cancelled images are obtained from the first and second energy level images according to a cancellation equation using the first and second cancellation parameters. In accordance with an alternative embodiment, the cancellation equation represents a relationship between the high and low energy images adjusted according to the first or second cancellation parameter.

In accordance with at least one alternative embodiment, a gradient mask is generated from a ratio of the high to low energy images where at least one of the images is adjusted based on the first or second cancellation parameter. In one embodiment, the high and low energy level images are compressed before generating the gradient mask. In another embodiment, a gradient image is generated based on the high and low energy image. The gradient image is then compared with a gradient threshold to form the gradient mask.

In accordance with at least one preferred embodiment, computing the characteristic mask further comprises creating a gradient image by convolving a Sobel operator with an image based on the low and high energy level images. A predetermined gradient threshold is automatically selected from a set based upon a selected diagnostic application and compared to the gradient image to create the gradient mask.

In accordance with at least one preferred embodiment, the characteristic mask is computed by comparing pixels of the gradient mask to corresponding pixels of the localization mask and assigning an identifier to the pixel of the characteristic mask if the corresponding pixels of the gradient mask and the localization mask are equal and a different identifier if the pixels are not equal. In an alternative embodiment, a first value is assigned to pixels in the characteristic mask representing one type of structure and a second value is assigned to pixels in the characteristic mask representing a second type of structure.

In accordance with at least one preferred embodiment, a series of gradient maps are generated utilizing the cancellation equation and high and low energy level images by adjusting the first cancellation parameter to a value having a maximum likelihood of emphasizing the first type of structure. In an alternative embodiment, the gradient maps are further computed using cancellation parameters from a look-up table, and the lowest gradient value and associated cancellation parameter for each pixel location is identified.

In accordance with at least one preferred embodiment, the cancellation parameter having the maximum likelihood of canceling the first type of structure is identified as the peak of a histogram comprised of the lowest gradient values. In an alternative embodiment, the cancellation parameter is identified by calculating the mean of the cancellation parameters associated with the lowest gradient values derived from the characteristic mask.

Figure 1:
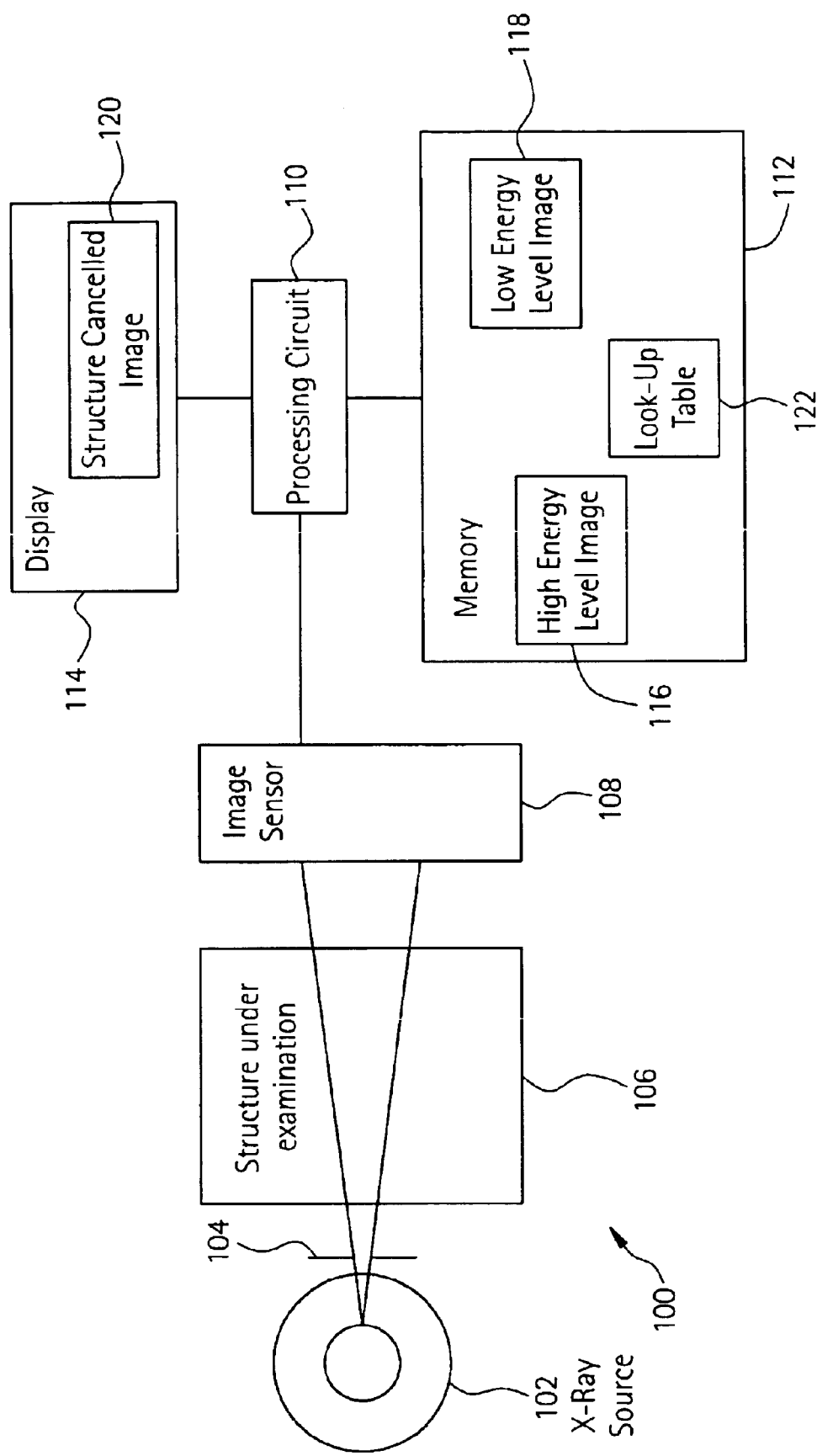
FIG. 1 illustrates a high level diagram of an X-ray imaging system in accordance with a preferred embodiment of the present invention.

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

DETAILED DESCRIPTION

With initial reference to FIG. 1, the figure illustrates an X-ray imaging system 100. The imaging system 100 includes an X-ray source 102 and a collimator 104 which subject structure under examination 106 to X-ray photons. By way of example, the X-ray source 102 may be an X-ray tube, and the structure under examination 106 may be a human patient, test phantom or other inanimate object under test.

The X-ray imaging system 100 also includes an image sensor 108, such as a flat panel solid state detector, coupled to a processing circuit 110. The processing circuit 110 (e.g., a microcontroller, microprocessor, custom ASIC, or the like) couples to a memory 112 and a display 114. The memory 112 (e.g., including one or more of a hard disk, floppy disk, CDROM, EPROM, and the like) stores a high energy level image 116 (e.g., an image read out from the image sensor 108 after 110–140 kVp exposure) and a low energy level image 118 (e.g., an image read out after 60–90 kVp exposure). The memory 112 also stores instructions for execution and a look-up table 122 of parameters used by the processing circuit 110, as explained below, to cancel certain types of structure in the images 116 and 118, such as hard structure (bone) or soft structure (tissue). One or more structure cancelled images 120 are thereby produced for display.

The processing circuit 110 uses a cancellation technique to decompose spatially registered images from the structure under examination 106 into constituent materials (e.g., bone and soft tissue in chest X-ray images). For example, a chest X-ray image may be decomposed to create one image representing hard structure, such as bone, and one image representing soft structure, such as lung.

Figure 2:
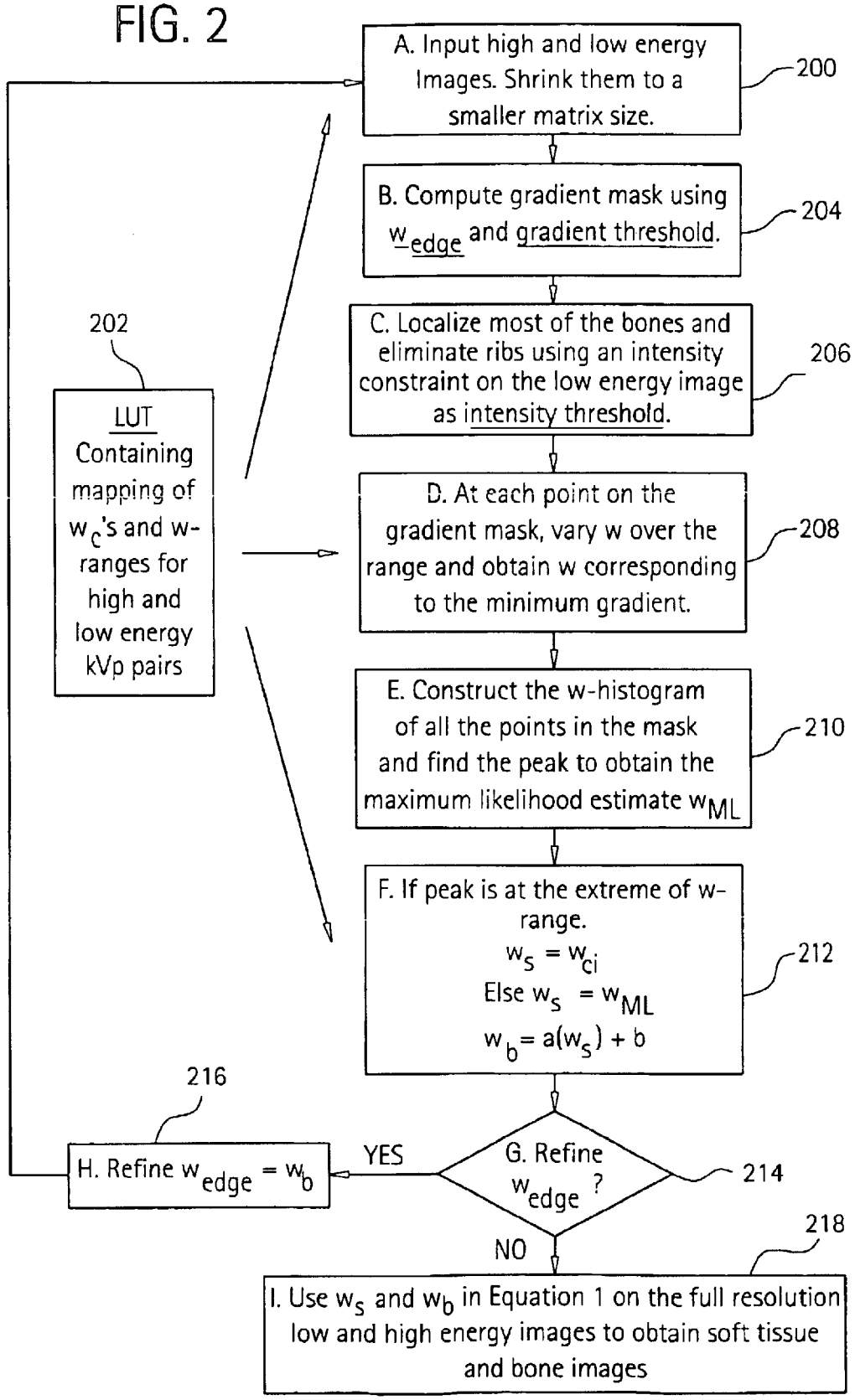
FIG. 2 illustrates a flow-chart of a process to decompose X-ray images in accordance with a preferred embodiment of the present invention.

FIG. 2 illustrates one exemplary processing sequence carried out by the x-ray imaging system 100. At step 200, a high energy level image 116 and a low energy level image 118 are acquired and stored in memory 112. The images 116 and 118 contain both hard and soft structure. In at least one preferred embodiment, the high energy level image 116 and the low energy level image 118 are reduced to a smaller matrix size. This reduction may be accomplished by neighborhood averaging and the like.

At step 204, the processing circuit 110 determines a parameter that is likely to extract one type of structure, mainly either soft or hard structure. In at least one preferred embodiment, the parameter may be a derived from a look-up table (LUT 122, also stored in memory 2, as shown below in Table 1:

TABLE 1

|      | H 110 | H 120 | H 130 | H 140 |
|------|-------|-------|-------|-------|
| L 90 |       |       |       | 0.66 [0.55, 0.75] |
| L 80 |       | 0.65 [0.55, 0.75] | 0.6 [0.5–0.7] | 0.55 [0.45, 0.65] |
| L 70 | 0.57 [0.45, 0.65] | 0.53 [0.43, 0.63] | 0.5 [0.4, 0.6] | $w_c$ = 0.48 w-range = [0.38, 0.58] |
| L 60 | 0.46 [0.35, 0.55] | 0.43 [0.33, 0.53] | 0.41 [0.31, 0.51] | 0.38 [0.28, 0.48] |

The low energy kVp levels are illustrated in the left column and the high energy kVp levels are illustrated in the bottom row. The kVp levels represent the effective kVp to the structure under examination 106, which may vary from the kVp level of the X-ray source 102. The variance may be due to the use of one or more filters used to modulate the kVp. The filter may be comprised of copper, aluminum, or other material or combination of materials and may be located near the collimator 104.

Table 1 is further comprised of parameters determined based on humanoid phantom studies or based on human patients at different kVp levels for high energy level images 116 and low energy level images 118. The numbers in Table 1 represent the parameter, $w_c$, that has a likelihood of canceling one of the types of structure (hereafter sometimes referred to as the cancellation parameter) and a range of parameters, w-range, that will be utilized to determine the parameter that may best cancel the second type of structure (hereafter sometimes referred to as the cancellation range). For example, if a low energy level image 118 is acquired with an effective kVp of 60 and a high energy level image 116 is acquired with an effective kVp of 110, Table 1 may be utilized to find the cancellation parameter $w_c$=0.46 and the cancellation range w-range=[0.35,0.55].

At step 204, the processing circuit 10 computes a gradient mask. First, in a preferred embodiment, an edge cancellation parameter w d is computed using the cancellation parameter $w_c$ from Table 1 in the following equation:

$$W_{edge} = (1+w_c)/2$$

Continuing the above example, the value of the cancellation parameter w is 0.46, thus the edge cancellation parameter $w_{edge}=0.73$. In an alternate embodiment, a predetermined cancellation parameter found to work well to extract one type of structure may be used. The predetermined parameter may be dependent upon the type of image being acquired. Next, in a preferred embodiment, the processing circuit 110 processes the edge cancellation parameter $w_{edge}$, the reduced high energy level image and the reduced low energy level image according to Equation 1 below:

$$I(x,y)=I_{HIGH}/(x,y)(I_{LOW}(x,y))^w \quad \text{(Equation 1)}$$

where w is $w_{edge}$, and $I_{HIGH}(x,y)$ and $I_{LOW}(x,y)$ are the pixels' intensity values of the reduced high and low energy level images. Equation 1 is much faster than the log subtraction equation previously utilized, and thus is an improved method of decomposing images.

The processing circuit 110 then computes a gradient using the result of Equation 1, decomposed image I(x,y). In a preferred embodiment, the gradients may be obtained by convolving a Sobel operator with decomposed image I(x,y). Next, the gradients are compared to a gradient threshold. The gradient threshold is a fixed value that is set based upon the application. In an embodiment of the present invention, the gradient threshold may be picked from a set of values based upon the application, such as chest, c-spine, and lumbar spine by way of example only. The gradient mask is created by assigning a first identifier (e.g. such as 1) to any pixel greater than the gradient threshold and a second identifier (e.g. such as 0) to any pixel less than the gradient threshold. The processing circuit 110 may store the gradient threshold in memory 112. At step 206, the processing circuit 110 creates a characteristic mask by computing a localization mask to identify the soft structure and comparing the localization mask to the gradient mask. To compute the localization mask, the low energy level image 118 is compared with an intensity threshold. In a preferred embodiment, the intensity threshold is based upon the average or mean intensity of the image. In an alternative embodiment, the intensity threshold is a fixed value based upon the application. The localization mask is created by assigning a first identifier (e.g. 1) to any pixel greater than the intensity threshold and a second identifier (e.g. 0) to any pixel less than the intensity threshold. The processing circuit 110 may store the localization mask in memory 112.

Figure 4:
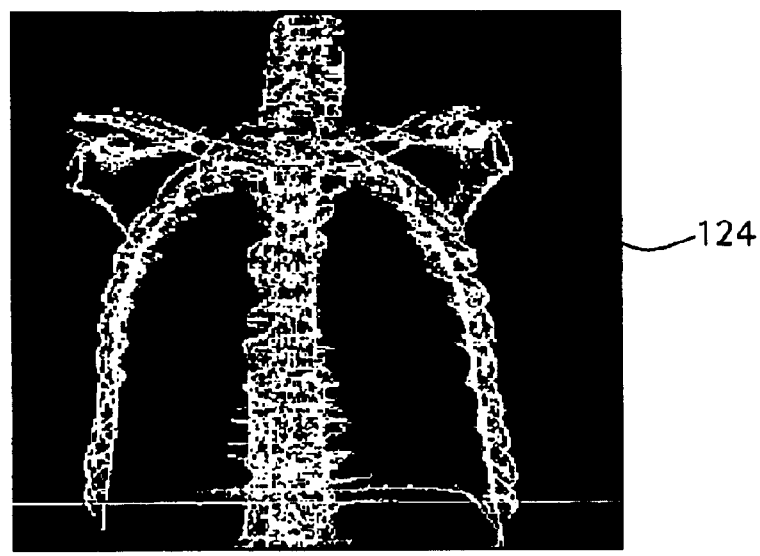
FIG. 4 illustrates a characteristic mask in accordance with a preferred embodiment of the present invention.

Next, processing circuit 110 computes a characteristic mask. FIG. 4 illustrates a characteristic mask 124. In a preferred embodiment of the present invention, the characteristic mask 124 is a binary mask in which the pixels representing the hard structure, or bone, are white, and the pixels representing the soft structure, or lungs, including the ribs, are black. The characteristic mask is computed by comparing the pixels of the gradient mask to the corresponding pixels of the localization mask. For pixel locations that contain the first identifier (e.g. 1) in both the gradient mask and the localization mask, the corresponding pixel location of the characteristic mask is assigned the second identifier (e.g. 0). For pixel locations that contain the first identifier (e.g. 1) in either the gradient mask or the localization mask but not both, the corresponding pixel location of the characteristic mask 124 is assigned the first identifier (e.g. 1). The characteristic mask 124 may be stored in memory 112.

At step 208, the processing circuit 110 identifies the minimum gradient at every pixel location of the characteristic mask containing the first identifier (e.g. 1). In a preferred embodiment, cancellation parameters from the LUT 122 and the high energy level image 116 and the low energy level image 118 are utilized in Equation 1 to obtain the decomposed image I(x,y). Continuing with the above example, the cancellation range w-range used in Equation 1 will be 0.35 0.55. Equation 1 is calculated at each pixel location corresponding to the pixel locations of the characteristic mask 124 containing the first identifier (e.g. 1). In one preferred embodiment, the first value of cancellation parameter w used in Equation 1 is 0.55. In an alternative embodiment, the first value of cancellation parameter w used in Equation 1 is 0.35.

Next, the gradient is computed for each decomposed image I(x,y) of Equation 1. In a preferred embodiment, the decomposed image I(x,y) is convolved with a Sobel operator to obtain the gradient at each point (x,y) of interest from the characteristic mask 124. The gradients and corresponding cancellation parameter w are recorded. In a preferred embodiment, each gradient and corresponding cancellation parameter w are stored in memory 112. In an alternative embodiment, the gradient and corresponding cancellation parameter w are stored as an image. The next set of gradients are now computed from decomposed image I(x,y) using the next parameter in the cancellation range w-range in Equation 1. In a preferred embodiment, the value of the cancellation parameter w is varied (e.g. increased or decreased) by 0.1, and the gradient is calculated at each point of interest in the new decomposed image I(x,y). The process is repeated for every cancellation parameter w over the cancellation range w-range. In an alternative embodiment, the cancellation parameter w is varied over the range and the gradients are calculated at predetermined intervals. The gradients at each pixel location are then compared to determine the lowest gradient and corresponding cancellation parameter w at each pixel (x,y) location.

Figure 3:
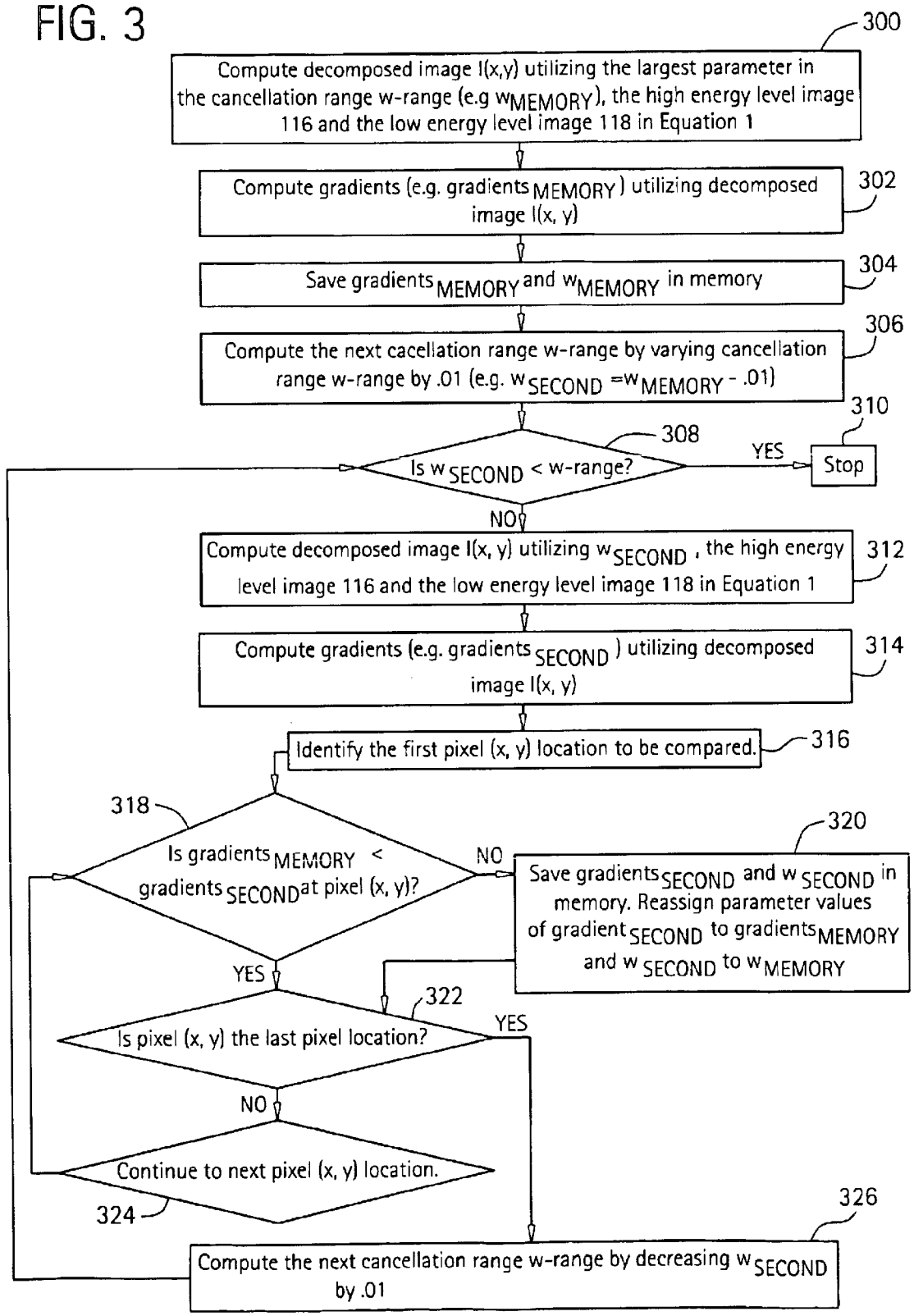
FIG. 3 illustrates a flow-chart of a method to determine the minimum gradient value at every pixel location of the characteristic mask in accordance with a preferred embodiment of the present invention.

FIG. 3 illustrates a preferred embodiment of the method the processing circuit 110 utilizes to determine the minimum gradient at every pixel location of the characteristic mask 124 containing the first identifier (e.g. 1). First, at step 300, the decomposed image I(x,y) is computed utilizing the largest parameter in the cancellation range w-range (hereafter sometimes referred to as $w_{MEMORY}$) the high energy level image 116 and the low energy level image 118 in Equation 1. Continuing with the above example, the value of $w_{MEMORY}$ is 0.55. Next, at step 302, the gradients (hereafter sometimes referred to as gradients $_{MEMORY}$) are calculated. This may be accomplished by convolving a Sobel operator with the decomposed image I(x,y). The gradients$_{MEMORY}$ and $w_{Memory}$ are then saved in memory 112 at step 304.

At step 306, the next value of cancellation range w-range (hereafter sometimes referred to as $w_{SECOND}$) to be used in Equation 1 is computed. As illustrated in FIG. 3 step 306, 0.01 is subtracted from $w_{MEMORY}$ ($w_{SECOND}=w_{MEMORY}-0.01$). Continuing with the above example, the parameter $w_{SECOND}$ is 0.54.

Step 308 makes sure that the value of $w_{SECOND}$ is within the cancellation range w-range. If $w_{SECOND}$ is less than the cancellation range w-range, control passes to step 310 and the processing circuit 110 returns to step 210 of FIG. 2.

If $w_{SECOND}$ is not less than the cancellation range w-range, control passes to step 312.

At step 312, $w_{SECOND}$ is utilized with the high energy level image 116 and the low energy level image 118 in Equation 1 to compute decomposed image I(x,y). Next, at step 314, the gradients (hereafter sometimes referred to as gradients $_{SECOND}$) are calculated. Again, this may be accomplished by convolving a Sobel operator with the decomposed image I(x,y). At step 316, the processing circuit 110 identifies the first pixel (x,y) to be compared. The step 318 asks: Is gradients$_{MEMORY}$<gradients$_{SECOND}$ at pixel (x,y)? If the answer to the question is no, control passes to step 320 and parameters gradients$_{SECOND}$ and w$_{SECOND}$ are stored in memory 112 and parameters gradients$_{MEMORY}$ and w$_{MEMORY}$ are discarded. Parameter gradients$_{MEMORY}$ is assigned the value of gradients $_{SECOND}$, and parameter w$_{MEMORY}$ is assigned the value of w$_{SECOND}$. If the answer to the question is yes, parameters gradients$_{MEMORY}$ and w$_{MEMORY}$ are stored in memory 112.

Next, step 322 asks: Is pixel (x,y) the last pixel location? If the answer is no, control passes to step 324 where the processing circuit 110 instructs to continue to the next pixel (x,y) location and return to step 318 to continue identifying the lowest gradients. If the answer is yes, the lowest gradient and corresponding cancellation parameter for each pixel has been stored in memory 112. Next, step 326 computes the next cancellation range w-range parameter by decreasing w $_{SECOND}$ by 0.01. Control passes to step 308, where the method continues to evaluate the gradients for every parameter of the cancellation range w-range.

In an alternative embodiment, the gradients are computed for each parameter in the cancellation parameter w-range and stored in memory 112. After all of the gradients have been computed, the gradients are compared at each pixel (x,y) location to identify the minimum gradient and corresponding w parameter.

Figure 5:
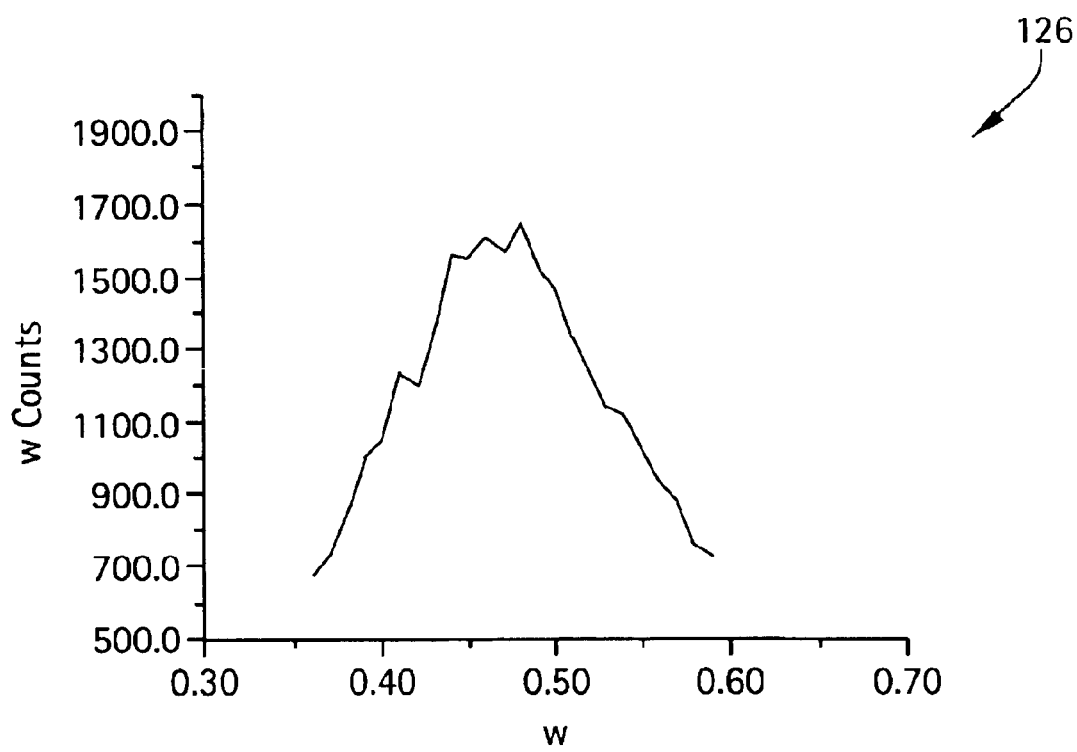
FIG. 5 illustrates a histogram of the quantity of w parameters with the lowest gradient values in accordance with a preferred embodiment of the present invention.

At step 210, the processing circuit 110 determines the initial cancellation parameter having the maximum likelihood of emphasizing the first type of structure. First, the cancellation parameters w identified above are used to calculate the total number of occurrences of each cancellation parameter w at the minimum gradient values, and the cancellation parameter w with the highest number of occurrences is identified as the maximum likelihood cancellation parameter w$_{ML}$. In a preferred embodiment of the present invention, the cancellation parameters w are used to create a histogram 126, as illustrated in FIG. 5. The number of occurrences of the cancellation parameter w are represented on the vertical axis and the corresponding cancellation parameters w are represented on the horizontal axis of the histogram 126. The maximum likelihood cancellation parameter w$_{ML}$ having the maximum likelihood of canceling the first type of structure is identified as the peak of the histogram 126. In an alternative embodiment, the mean or average value of the cancellation parameters w may be used to identify the maximum likelihood cancellation parameter w$_{ML}$.

At step 212, the processing circuit 110 calculates the parameter with the maximum likelihood of canceling the first type of structure w$_s$ and the parameter with the maximum likelihood of canceling the second type of structure w$_b$. First, the maximum likelihood parameter w$_{ML}$ identified in block 210 is evaluated. It is possible that an error may have occurred during the acquisition of the high energy level image 116 or the low energy level image 118, or during the subsequent processing of the image which may cause maximum likelihood parameter w$_{ML}$ to be invalid. In a preferred embodiment, the histogram 126 is evaluated to determine whether the peak of the histogram 126 is at either extreme edge of the cancellation range w-range. If the peak is at either extreme edge of the cancellation range w-range, then the parameter with the maximum likelihood of canceling the first type of structure w is equal to the cancellation parameter w$_c$ (e.g. w$_s$=w$_c$). If the peak of the histogram 126 is in the central area of the histogram 126, then the parameter with the maximum likelihood of canceling the first type of structure w$_s$ is equal to the maximum likelihood cancellation parameter w$_{ML}$ (e.g. w$_s$=w$_{ML}$) Next, the parameter with the maximum likelihood of canceling the second type of structure w$_b$ is calculated using the parameter with the maximum likelihood of canceling the first type of structure w$_s$ in the following linear relationship:

$$W_b = a(W_s) + b$$

where a and b are constants. In a preferred embodiment, a=b=0.5.

At step 214, the processing circuit 110 determines whether to recalculate the parameter with the maximum likelihood of canceling the first type of structure w$_s$ and the parameter with the maximum likelihood of canceling the second type of structure w$_b$. In an embodiment of the present invention, the decision is made to refine the edge cancellation parameter w$_{edge}$ and recalculate the parameter with the maximum likelihood of canceling the first type of structure w$_s$ and parameter with the maximum likelihood of canceling the second type of structure w$_b$. Control passes to step 216, where the processing circuit assigns the edge cancellation parameter w$_{edge}$ the value of the parameter with the maximum likelihood of canceling the second type of structure w$_b$ (w$_{edge}$=w$_b$) Next, the method returns to step 204 and repeats the steps described above. If the value of the maximum likelihood cancellation parameter w$_{ML}$ at step 210 does not change, there is no need to further refine the maximum likelihood cancellation parameter w$_{edge}$. In a preferred embodiment, step 214 is optional and the parameters with the maximum likelihood of canceling the first type of structure w$_s$ and second type of structure w$_b$ are not recalculated. Instead, control passes to step 218.

Figure 6:
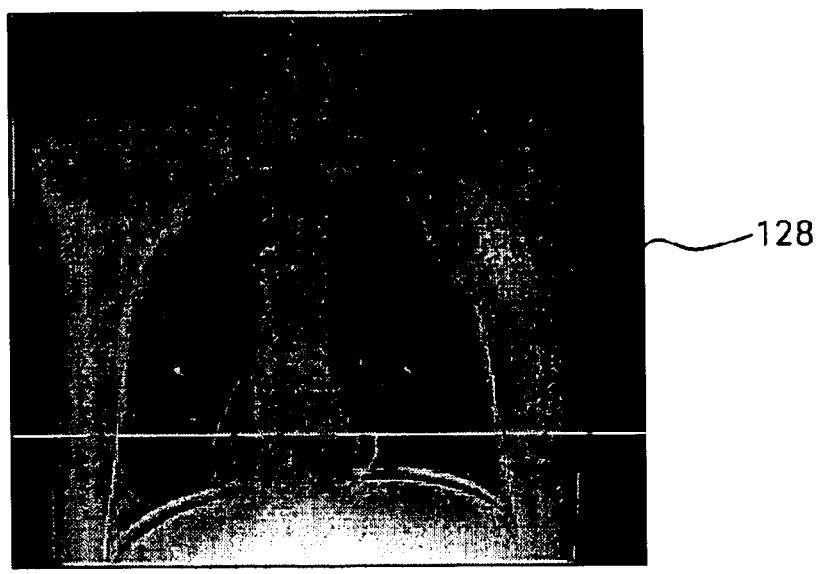
FIG. 6 illustrates the soft structure decomposed image in accordance with a preferred embodiment of the present invention.
Figure 7:
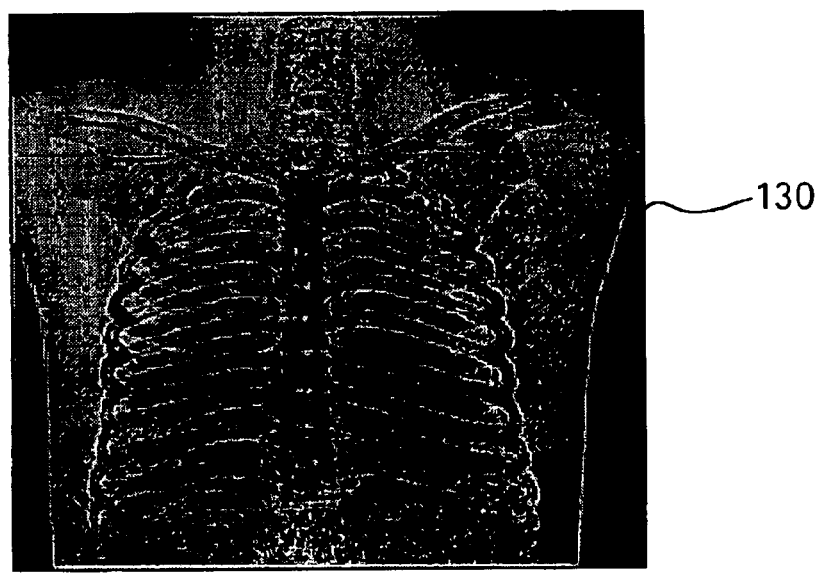
FIG. 7 illustrates the hard structure decomposed image in accordance with a preferred embodiment of the present invention.

At step 218, the processing circuit 110 creates the decomposed images 128 and 130. The parameter with the maximum likelihood of canceling the first type of structure w$_s$ and second type of structure w$_b$ are used in Equation 1 with the original high energy level image 116 and low energy level image 118. Using the value of the parameter with the maximum likelihood of canceling the first type of structure w$_s$ in Equation 1 as shown below:

$$L(x,y) = I_{HIGH}(x,y)/(I_{LOW}(x,y))^{ws}$$

will result in an image of soft structure 128, as illustrated in FIG. 6. Using the parameter with the maximum likelihood of canceling the second type of structure w$_b$ in Equation 1 as shown below:

$$I_b(x,y) = I_{HIGH}(x,y)/(I_{LOW}(x,y))^{wb}$$

will result in an image of hard structure 130, as illustrated in FIG. 7.

Having the values of the cancellation parameter w$_c$ and the cancellation range w-range empirically determined and available in the LUT 122 can improve the performance of image decomposition. As the method illustrated in FIG. 2 utilizes the predetermined parameters, such as cancellation parameter w$_c$, cancellation range w-range, gradient threshold, intensity threshold and the like, input from the operator is not necessary and the time required to complete the calculations is reduced. The method tests the cancellation range w-range and determines the maximum likelihood cancellation parameter w$_{ML}$ through comparison of the gradient values at each pixel (x,y). The method Is not subject to possible operator biases, thus, the parameters with the maximum likelihood of canceling the first type of structure w$_s$ and second type of structure w$_b$ determined by the method will be the parameters that provides the best cancellation of the chosen structure.

While the invention has been described with reference to a preferred embodiment, those skilled in the art will understand that various changes may be made and equivalents may be substituted without departing from the scope of the invention. In addition, many modifications may be made to adapt a particular step, structure, or material to the teachings of the invention without departing from its scope. Therefore, it is intended that the invention not be limited to the particular embodiment disclosed, but that the invention will include all embodiments falling within the scope of the appended claims.

What is claimed is:

1. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

computing a characteristic mask using the low energy level image and by comparing one or more pixels of a gradient mask to one or more corresponding pixels of a localization mask;

evaluating a first cancellation parameter against the characteristic mask;

computing a second cancellation parameter based on the first cancellation parameter; and obtaining a structure cancelled image from the first and second energy level images according to a cancellation equation using one of the first and second cancellation parameter.

2. The method of claim 1, wherein the cancellation equation represents a relationship between the high energy image and the low energy image adjusted according to the first or second cancellation parameter.

3. The method of claim 1, wherein the first or second cancellation parameter is selected from a predetermined range in a look-up table, the range being determined by an effective kVp used to acquire the high level image and an effective kVp used to acquire the low level image.

4. The method of claim 1, wherein the computing the characteristic mask step further comprises:

assigning a first value to pixels representing only hard structure in the low energy level image; and assigning a second value to pixels representing only soft structure in the low energy level image.

5. The method of claim 1, further comprising:

computing a hard structure cancelled image and a soft structure cancelled image using the cancellation equation, the first cancellation parameter and the second cancellation parameter.

6. The method of claim 1, wherein the second cancellation parameter is linearly related to the first cancellation parameter.

7. The method of claim 1, wherein said step of obtaining a structure cancelled image further comprises:

obtaining a first structure cancelled image from the first and second energy level images according to the cancellation equation using the first cancellation parameter; and obtaining a second structure cancelled image according to the cancellation equation using the second cancellation parameter.

8. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

generating a gradient mask from a ratio of the high to low energy images, at least one of the high and low energy images being adjusted based on first or second cancellation parameters, wherein the gradient mask is used when automatically computing the first or second cancellation parameters;

computing a characteristic mask using the low energy level image;

evaluating the first cancellation parameter against the characteristic mask;

computing the second cancellation parameter based on the first cancellation parameter; and obtaining a structure cancelled image from the first and second energy level images according to a cancellation equation using one of the first and second cancellation parameter.

9. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

compressing the high and low energy level images used to generate the gradient masks;

generating a gradient mask from a ratio of the high to low energy images, at least one of the high and low energy images being adjusted based on the first or second cancellation parameters, wherein the gradient mask is used when automatically computing the first or second cancellation parameter;

computing a characteristic mask using the low energy level image;

evaluating the first cancellation parameter against the characteristic mask;

computing the second cancellation parameter based on the first cancellation parameter; and obtaining a structure cancelled image from the first and second energy level images according to a cancellation equation using one of the first and second cancellation parameter.

10. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

generating a gradient image based on the high and low energy images;

comparing the gradient image with a gradient threshold to form a gradient mask, wherein the gradient mask is used when automatically computing the first or second cancellation parameters;

computing a characteristic mask using the low energy level image;

evaluating a first cancellation parameter against the characteristic mask;

computing a second cancellation parameter based on the first cancellation parameter; and obtaining a structure cancelled image from the first and second energy level images according to a cancellation equation using one of the first and second cancellation parameter.

11. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

computing a characteristic mask using the low energy level image;

evaluating a first cancellation parameter against the characteristic mask;

computing a second cancellation parameter based on the first cancellation parameter; and obtaining a structure cancelled image from the first and second energy level images according to a cancellation equation using one of the first and second cancellation parameter;

wherein said step of computing a characteristic mask further comprises:

convolving a Sobel operator with an image based on the low energy level and the high energy level images to form a gradient image;

selecting a predetermined gradient threshold automatically from a set based upon a selected diagnostic application; and creating the gradient mask by comparing the gradient image to the gradient threshold and assigning a first identifier to any image pixel greater than the gradient threshold and a second identifier to any image pixel less than the gradient threshold.

12. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

computing a characteristic mask using the low energy level image;

evaluating a first cancellation parameter against the characteristic mask;

computing a second cancellation parameter based on the first cancellation parameter; and obtaining a structure cancelled image from the first and second energy level images according to a cancellation equation using one of the first and second cancellation parameter, wherein the cancellation equation is:

$$I_s(x,y) = I_{HIGH}(x,y))^{w_s}$$

and $w_s$ is the first cancellation parameter, $I_{HIGH}$ is the high energy level image, and $I_{LOW}$ is the low energy level image.

13. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

computing a characteristic mask using the low energy level image;

evaluating a first cancellation parameter against the characteristic mask;

computing a second cancellation parameter based on the first cancellation parameter; and obtaining a structure cancelled image from the first and second energy level images according to a cancellation equation using one of the first and second cancellation parameter, wherein the cancellation equation is:

$$I_b(x,y) = I_{HIGH}(x,y)/(I_{LOW}(x,y))^{w_b}$$

and $w_b$ is the second cancellation parameter, $I_{HIGH}$ is the high energy level image, and $I_{LOW}$ is the low energy level image.

14. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

generating a localization image based on the low energy image;

comparing the localization image with an intensity threshold to form a localization mask, wherein the localization mask is used when automatically computing first or second cancellation parameters;

computing a characteristic mask using the low energy level image;

evaluating the first cancellation parameter against the characteristic mask;

computing the second cancellation parameter based on the first cancellation parameter; and obtaining a structure cancelled image from the first and second energy level images according to a cancellation equation using one of the first and second cancellation parameter.

15. A method for automatically determining a structure cancelled image in a dual energy decomposition system, the method comprising:
  obtaining a first high energy level image of internal anatomy formed of at least first and second types of structure;
  obtaining a second low energy level image of the internal anatomy formed of at least the first and second types of structure at an energy level lower than the first energy level image;
  generating a localization image based on the low energy image;
  comparing the localization image with an intensity threshold to form a localization mask, wherein the localization mask is used when automatically computing first or second cancellation parameters;
  computing a characteristic mask using the low energy level image;
  evaluating the first cancellation parameter against the characteristic mask;
  computing the second cancellation parameter based on the first cancellation parameter; and
  obtaining a structure cancelled image from the first and second energy level images according to a cancellation equation using one of the first and second cancellation parameter;
  wherein the comparing step further comprises:
    selecting the predetermined intensity threshold automatically from a set based upon said selected diagnostic application.

16. A method for automatically determining a structure cancelled image in a dual energy decomposition system, the method comprising:
  obtaining a first high energy level image of internal anatomy formed of at least first and second types of structure;
  obtaining a second low energy level image of the internal anatomy formed of at least the first and second types of structure at an energy level lower than the first energy level image;
  computing a characteristic mask using the low energy level image;
  evaluating a first cancellation parameter against the characteristic mask;
  computing a second cancellation parameter based on the first cancellation parameter; and
  obtaining a structure cancelled image from the first and second energy level images according to a cancellation equation using one of the first and second cancellation parameter,
  wherein the step of computing the characteristic mask further comprises;
    computing a gradient mask;
    computing a localization mask; and
    creating the characteristic mask by comparing pixels of the gradient mask to corresponding pixels of the localization mask and assigning a second identifier to the corresponding pixel of the characteristic mask if the corresponding pixels of the gradient mask and the localization mask are equal.

17. A method for automatically determining a structure cancelled image in a dual energy decomposition system, the method comprising:
  obtaining a first high energy level image of internal anatomy formed of at least first and second types of structure;
  obtaining a second low energy level image of the internal anatomy formed of at least the first and second types of structure at an energy level lower than the first energy level image;
  computing a characteristic mask using the low energy level image;
  evaluating a first cancellation parameter against the characteristic mask;
  computing a second cancellation parameter based on the first cancellation parameter; and
  obtaining a structure cancelled image from the first and second energy level images according to a cancellation equation using one of the first and second cancellation parameter,
  wherein the evaluating step further comprises:
    generating a series of gradient maps utilizing the cancellation equation and high and low energy level images by adjusting the first cancellation parameter to a value having a maximum likelihood of emphasizing the first type of structure.

18. A method for automatically determining a structure cancelled image in a dual energy decomposition system, the method comprising:
  obtaining a first high energy level image of internal anatomy formed of at least first and second types of structure;
  obtaining a second low energy level image of the internal anatomy formed of at least the first and second types of structure at an energy level lower than the first energy level image;
  computing a characteristic mask using the low energy level image;
  evaluating a first cancellation parameter against the characteristic mask;
  computing a second cancellation parameter based on the first cancellation parameter; and
  obtaining a structure cancelled image from the first and second energy level images according to a cancellation equation using one of the first and second cancellation parameter,
  wherein the evaluating step further comprises:
    computing multiple gradient maps using a range of cancellation parameters from a look up table; and
    determining a lowest gradient value for each pixel location by comparing corresponding pixel locations of the multiple gradient maps to each other and identifying an associated cancellation parameter for each of the identified lowest gradient values.

19. A method for automatically determining a structure cancelled image in a dual energy decomposition system, the method comprising:
  obtaining a first high energy level image of internal anatomy formed of at least first and second types of structure;
  obtaining a second low energy level image of the internal anatomy formed of at least the first and second types of structure at an energy level lower than the first energy level image;
  computing a characteristic mask using the low energy level image;
  evaluating a first cancellation parameter against the characteristic mask;
  computing a second cancellation parameter based on the first cancellation parameter;

creating a histogram comprised of cancellation parameters associated with the lowest gradient values derived from the characteristic mask;

identifying a cancellation parameter occurring at the peak of the histogram as the value of the cancellation parameter having the maximum likelihood of canceling the first type of structure; and obtaining a structure cancelled image from the first and second energy level images according to a cancellation equation using one of the first and second cancellation parameter, wherein the evaluating step further comprises:

computing multiple gradient maps using a range of cancellation parameters from a look up table; and determining a lowest gradient value for each pixel location by comparing corresponding pixel locations of the multiple gradient maps to each other and identifying an associated cancellation parameter for each of the identified lowest gradient values.

20. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

computing a characteristic mask using the low energy level image;

evaluating a first cancellation parameter against the characteristic mask;

computing a second cancellation parameter based on the first cancellation parameter;

identifying a value of the cancellation parameter having the maximum likelihood of emphasizing the first type of structure by calculating a mean of the cancellation parameters associated with the lowest gradient values derived from the characteristic mask; and obtaining a structure cancelled image from the first and second energy level images according to a cancellation equation using one of the first and second cancellation parameter, wherein the evaluating step further comprises:

computing multiple gradient mans using a range of cancellation parameters from a look up table; and determining a lowest gradient value for each pixel location by comparing corresponding pixel locations of the multiple gradient maps to each other and identifying an associated cancellation parameter for each of the identified lowest gradient values.

21. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

computing a gradient mask identifying a characteristic of interest from the internal structure based on a predefined cancellation parameter;

localizing the characteristic of interest from the gradient mask based on a constraint parameter to form a characteristic mask;

at selected pixel locations in the characteristic mask, varying the cancellation parameter over a range and obtaining for each selected pixel the cancellation parameter value yielding a desired characteristic mask value; and determining a maximum likelihood estimate of a single value for the cancellation parameter.

22. The method of claim 21, wherein the computing step includes computing the gradient mask for the first and second energy level images using an edge cancellation parameter and a gradient threshold.

23. The method of claim 21, wherein the localizing step is based on an intensity threshold placed on the second energy level image.

24. The method of claim 21, wherein the varying step includes incrementally stepping the cancellation parameter between upper and lower parameter limits and, at each discrete value for the cancellation parameter, calculating a gradient value.

25. The method of claim 21, further comprising:

constructing a histogram of all pixel locations of interest from the characteristic mask.

26. A method for automatically determining a structure cancelled image in a dual energy decomposition system, the method comprising:

obtaining a first high energy level image of internal anatomy formed of at least first and second types of structure;

obtaining a second low energy level image of the internal anatomy formed of at least the first and second types of structure at an energy level lower than the first energy level image;

automatically computing a cancellation parameter having a maximum likelihood of canceling one of the first and second types of structure from a structure cancelled image based on a characteristic mask computed using the low energy level image and by comparing one or more pixels of a gradient mask to one or more corresponding pixels of a localization mask; and generate the structure cancelled image based on a cancellation equation using the automatically computed cancellation parameter, the structure cancelled image emphasizing the first types of structure and de-emphasizing the second type of structure.

27. The method of claim 26, wherein said computing step includes storing a first identifier at each pixel location corresponding to the first type of structure.

28. The method of claim 26, wherein said computing step includes storing a pattern of pixel values defining an image outline for the first type of structure.

* * * * *